United States Patent
Calman et al.

(10) Patent No.: US 9,962,814 B2
(45) Date of Patent: **\*May 8, 2018**

(54) FILAMENT TAPE UTILIZATION DEVICE

(71) Applicant: Geek Wraps, Inc., Oakland Park, FL (US)

(72) Inventors: Kenneth J. Calman, Fort Lauderdale, FL (US); Kathryn S. Calman, Fort Lauderdale, FL (US)

(73) Assignee: Geek Wraps, Inc., Oakland Park, FL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/470,608

(22) Filed: Mar. 27, 2017

(65) Prior Publication Data

US 2017/0197297 A1    Jul. 13, 2017

Related U.S. Application Data

(63) Continuation-in-part of application No. 13/929,765, filed on Jun. 27, 2013, now Pat. No. 9,604,347.

(60) Provisional application No. 61/690,477, filed on Jun. 27, 2012.

(51) Int. Cl.
*B25B 9/02*     (2006.01)
*B25B 27/00*    (2006.01)
*A61B 17/30*    (2006.01)

(52) U.S. Cl.
CPC ............ *B25B 9/02* (2013.01); *B25B 27/00* (2013.01); *A61B 17/30* (2013.01)

(58) Field of Classification Search
CPC .......... A61B 17/30; B25B 9/02; B25B 27/00; Y10T 29/53991; Y10T 29/49822; Y10T 156/1168; Y10T 156/12
See application file for complete search history.

(56) References Cited

U.S. PATENT DOCUMENTS

| | | | | |
|---|---|---|---|---|
| 3,653,389 A | * | 4/1972 | Shannon | A61B 17/30 294/99.2 |
| 4,005,893 A | * | 2/1977 | Tash | A47J 43/283 294/118 |
| 4,750,771 A | * | 6/1988 | Emmett | A61B 17/30 15/104.001 |
| 6,866,314 B2 | * | 3/2005 | Cho | A61B 17/30 294/25 |

* cited by examiner

*Primary Examiner* — Mark A Osele
*Assistant Examiner* — Christopher C Caillouet
(74) *Attorney, Agent, or Firm* — Ice Miller LLP

(57) ABSTRACT

A tool is provided having at least one handle, at least one tread, a wall, and a tread cover. The at least one handle includes a first surface, a second surface opposite the first surface, a first end, and a second end opposite the first end. The at least one tread is disposed at the first surface and the first end and includes at least one peak extending above the first surface and across the at least one handle. The wall extends from the second surface and originates at the first end. The tread cover is disposed over the at least one tread. The at least one tread and the wall define the first end.

20 Claims, 12 Drawing Sheets

FILAMENT TAPE UTILIZATION DEVICE

RELATED APPLICATION DATA

This application is a continuation-in-part of U.S. patent application Ser. No. 13/929,765, now U.S. Pat. No. 9,604, 347, which claims priority benefit of U.S. Provisional Application No. 61/690,477 filed Jun. 27, 2012, all of which are hereby incorporated in their entirety herein by reference.

FIELD OF THE DISCLOSURE

The present disclosure relates to the application and use of cutting filaments for use in applying adhesive sheet material, and, more particularly, a device and method for initiating cuts with cutting filaments.

BACKGROUND

Adhesive sheet materials are becoming the increasingly popular choice for advertising or otherwise displaying graphics on signs, automobiles, buildings, and numerous other surfaces. Adhesive sheet materials typically have a display side bearing desired graphics, colors, texture, images, and/or text and an application side that is coated with an adhesive substance and allows for application to various surfaces. The adhesive sheet material is typically applied in oversized sections and then cut to the desired shape and size.

One type of adhesive sheet material, which is commonly used in the vehicle wrap industry is vinyl paint wraps. Although vinyl paint wraps are common, vehicles can be customized using a variety of adhesive sheet materials and the customization can include, but is not limited to including, body color change and/or texture change.

The adhesive sheet material is applied to surfaces that have a variety of unique features, such as contours, edges, and elements such as handles or windows. It is desirable to shape the adhesive sheet material around the surfaces' unique features. Additionally, it is desirable to cut the adhesive sheet material to create design patterns and elements on the surfaces.

Traditionally, after applying a large section adhesive sheet material, the adhesive sheet material was cut to the desired shape and size using a razorblade or knife. When using a razorblade or knife to cut the adhesive sheet material, it is easy accidentally to cut or scratch the underlying surface. In order to avoid cutting or scratching the underlying surface, the operator may cut the adhesive sheet material by using a cutting filament. Cutting filaments are increasingly becoming the popular choice in adhesive sheet material application.

Typically, the cutting filament is secured to a main web with an adhesive base (collectively "filament tape"). The filament tape is applied to various surfaces in a desired shape or pattern. The adhesive sheet material is then placed on top of the filament tape. The cutting filament is then separated from the main web and pulled through the adhesive sheet material creating an incision in the adhesive sheet material in the desired shape or pattern. The excess adhesive sheet material and main web are then removed from the surface.

Currently, the art lacks a reliable and desirable apparatus and method for releasing and/or separating the cutting filament from the main web. Often the operator must invert and carefully cut the main web from the cutting filament using scissors, a razorblade, or a knife. This process is time consuming, cumbersome, and can require multiple attempts if, for example, the cut is too shallow leaving the main web intact or the cut is too deep trimming the cutting filament as well as the main web.

Accordingly, there is a need for a tool and a method to facilitate the initiation of the release and/or separation of the cutting filament from the main web.

BRIEF SUMMARY

In accordance with an embodiment of the present disclosure, a tool is provided having at least one handle, at least one tread, a wall, and a tread cover. The at least one handle includes a first surface, a second surface opposite the first surface, a first end, and a second end opposite the first end. The at least one tread is disposed at the first surface and the first end and includes at least one peak extending above the first surface and across the at least one handle. The wall extends from the second surface and originates at the first end. The tread cover is disposed over the at least one tread. The at least one tread and the wall define the first end.

In accordance with an embodiment of the present disclosure, a tool is provided having at least one handle, at least one tread, and a tread cover. The at least one handle includes a handle width, a first surface, a second surface opposite the first surface, a first end, and a second end opposite the first end. The at least one tread is disposed at the first surface and the first end and extends above the first surface and across the handle width. The tread cover is disposed over the at least one tread. The at least one tread and the tread cover define the first end.

BRIEF DESCRIPTION OF THE DRAWINGS

The embodiments described herein and other features, advantages, and disclosures contained herein, and the manner of attaining them, will become apparent and the present disclosure will be better understood by reference to the following description of various exemplary embodiments of the present disclosure taken in conjunction with the accompanying drawing, wherein.

Figure 1:
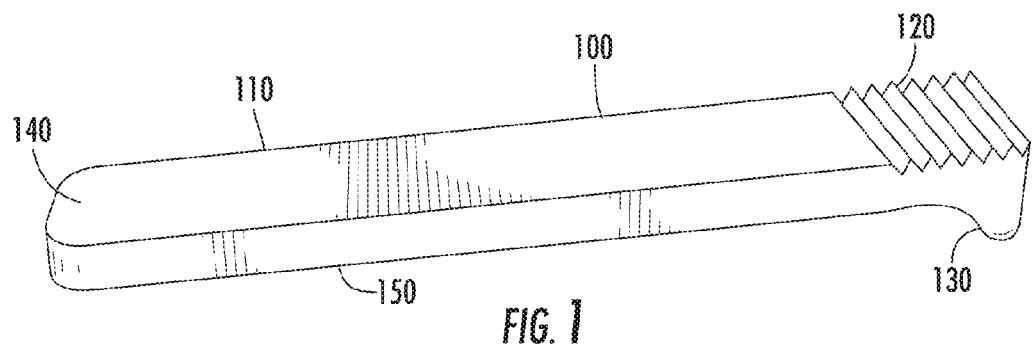
FIG. 1 is a perspective view of a filament tape utilization device according to at least one embodiment of the present disclosure.

It should be understood that the appended drawings are not necessarily to scale, presenting a somewhat simplified representation of various preferred features illustrative of the basic principles of the disclosure. Certain features of the illustrated embodiments have been enlarged or distorted relative to others to facilitate visualization and clear understanding. In particular thin features may be thickened, for example, for clarity or illustration.

DETAILED DESCRIPTION

For the purposes of promoting an understanding of the principles of the present disclosure, reference will be made to the embodiments illustrated in the drawings, and specific language will be used to describe the same. It will nevertheless be understood that no limitation of the scope of this disclosure is thereby intended.

Figure 2:
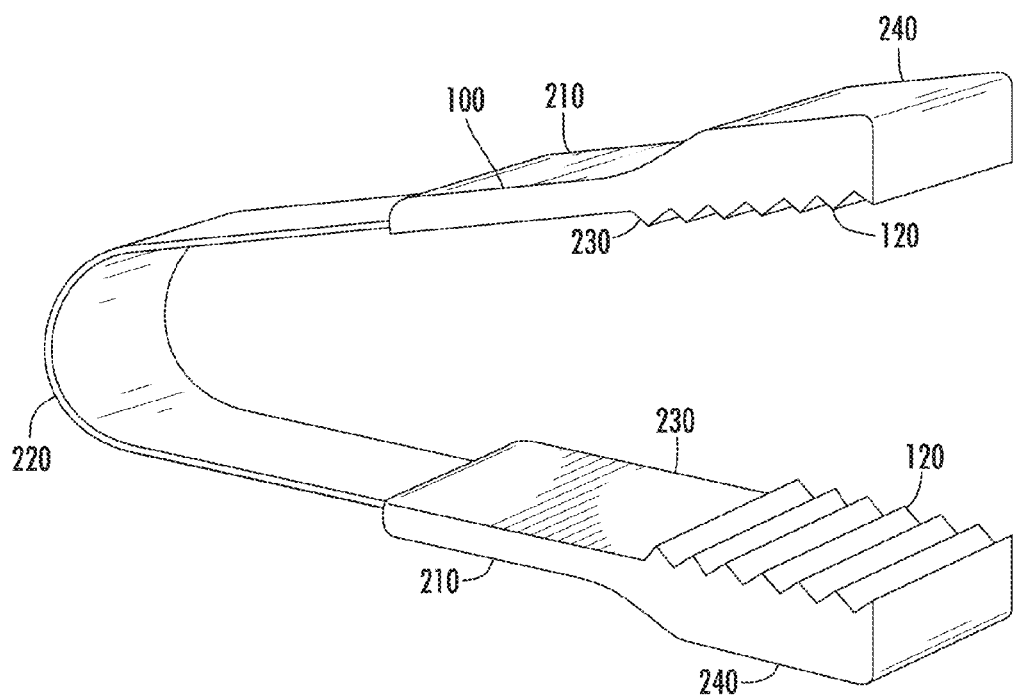
FIG. 2 is a perspective view of a filament tape utilization device according to at least one embodiment of the present disclosure.

The present application discloses various filament tape utilization devices and methods for using the same. FIG. 1 shows a perspective view of a filament tape utilization device 100 according to at least one embodiment of the present disclosure. FIG. 2 shows a perspective view of a filament tape utilization device 100 according to at least one embodiment of the present disclosure. As shown in FIGS. 1 and 2, the filament tape utilization device 100 is made up of one or more types of material including, but not limited to, rubber, silicone, metal, wood, leather, plastic, bioplastic and/or a polymer. The filament tape utilization device can be made of any strong flexible material that is capable of being shaped into a usable configuration. In one embodiment of the filament tape utilization device 100, the surface of the filament tape utilization device 100 is textured to allow for additional traction when held in a user's hand. The texture can be, but is not limited to being, tacky, ruff, sticky, grainy, coarse, and/or gritty. In another embodiment, only the handle 110 is textured.

As shown in FIG. 1, the filament tape utilization device 100 has a handle 110 to allow a user to hold the filament tape utilization device 100. The handle 110 can be a variety of shapes including, but not limited to, round, cylindrical, rectangular, flat, curved, and/or a combination of shapes. In one embodiment, the handle 110 is ergonomic. In another embodiment, the handle 110 has an outer layer, which is pliable and/or textured for added comfort and control.

As shown in FIG. 1, the handle 110 has a first surface 140 and a second surface 150 and a first end and a second end. At the first end of the second surface 150 there is a support wall 130, which can be used to support a user's hand and prevent the user's hand from sliding. The support wall 130 can be, but is not limited to being, curved or straight. The support wall 130 can be, but is not limited to being, long or short and as wide as, wider than, or less wide than the handle 110. In one embodiment the support wall 130 extends form the second surface between 0.25 and one inches. In one embodiment, the support wall 130 is located between the first and second ends of the handle 110. In another embodiment, the filament tape utilization device 100 does not have a support wall 130. In one embodiment, as shown in FIG. 1, the surface of the first surface 140 above the support wall 130 has treads 120. In another embodiment, the filament tape utilization device 100 has both treads and a support wall, only a support wall, only treads, or neither. The treads 120 can be, but are not limited to being, multiple peaks where each peak extends the entire width of the handle 110 and each peak rises slightly above the first surface 140. In one embodiment, there is only one tread 120. In one embodiment, the treads extend off the first surface between 0.04 and 0.2 inches. The treads 120 create pressure points where the main web 310 of the filament tape 300 can be sheared away from the cutting filament 310, as explained in more detail below. In another embodiment, the treads 120 can be a variety of textured surfaces, such as cones, grooves, ripples, bumps, spikes, or shards. As shown in FIG. 1, the treads 120 start at the first end of the first surface 140 and extend less than a quarter of the length of handle 110. In other embodiments, the distance the treads 120 extend from either the first or second end of the first surface 140 may vary. In one embodiment, the treads 120 are located between the first and second ends of the handle 110.

As shown in FIG. 2, in another embodiment of the present disclosure, the filament tape utilization device 100 has two handles 210. The two handles 210 are connected by a hinge 220. The hinge 220 can be, but is not limited to being, a flexible material, pivot hinge, or other suitable hinge known in the art. The hinge 220 may also include a locking mechanism that allows a user to lock the two handles 210 certain distances from each other. The hinge 220 allows the two handles 210 to mate at the end of the filament tape utilization device 100 opposite the hinge 220. The handle 210 has an inner handle 230 and an outer handle 240. On the inner handle 230 at the end of the handle 210 opposite the hinge 220 there are treads 120. The treads 120 on the two handles 210 will mate when the hinge 220 is in the closed position. In another embodiment, only one of the two handles 210 has treads 120. The outer handle 240 allows for a user's hand to hold and use the filament tape utilization device 100. The handle 210 can be a variety of shapes including, but not limited to, round, cylindrical, rectangular, flat, curved, and/or a combination of shapes. In one embodiment, the handle 210 is ergonomic. In another embodiment, the handle 210 has an outer handle 240, which is pliable and/or textured for added comfort and control. In yet another embodiment, the hinge 220 allows for rotation of the two handles 210 away from each other so that one handle 210 can be used alone.

Though the filament tape utilization device 100 as depicted in FIGS. 1 and 2 is a single part, in at least one embodiment, the filament tape utilization device 100 may comprise more than one part, for example, a handle 110 and separate clip-on treads 120 or support wall 130.

Figure 3A:
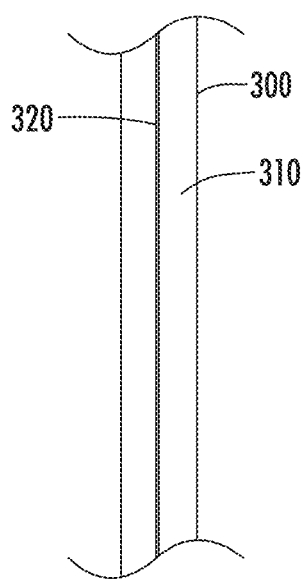
FIG. 3A is a front view of a section of a filament tape for use while installing adhesive sheet material.
Figure 3B:
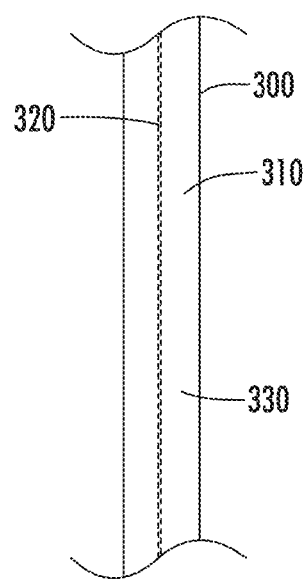
FIG. 3B is a back view of the section of the filament tape.

FIGS. 3A and 3B illustrate one type of filament tape 300 that can be used to cut or trim the adhesive sheet material 720, as explained in more detail below. Filament tape 300 is well known and used in a wide variety of industries. The present disclosure of a type of filament tape 300 is included only to aid in the understanding of one embodiment of the present disclosure. The types of filament tape 300 or similar products that the filament tape utilization device 100 can be used with includes, but is not limited to, a variety of designs and products that are currently available to the public and those, which are not yet available but have a similar application and design to the currently available filament tape 300. FIG. 3A shows the top of the filament tape 300 and FIG. 3B shows the bottom of the filament tape 300. As shown in FIGS. 3A and 3B, the filament tape 300 includes a main web 310 with a cutting filament 320 embedded in the main web 310, opposite the filament tape adhesive 330. In one embodiment, the filament tape adhesive 330 can be a substance applied or affixed to the main web 310. In another embodiment, the filament tape adhesive can be an integral part of the main web 310. The filament tape adhesive 300 allows the tape to temporarily adhere to the surface 710, as explained in more detail below. In other embodiments, the filament tape 300 can be a variety of sizes, textures, and assemblies. The filament tape utilization device 100 can be used with a variety of filament tape 300.

In other embodiments of the filament tape 300, the cutting filament 320 and main web 310 can have a wide variety of configurations. For example, the cutting filament 320 can be entirely encased in the main web 310, the cutting filament 320 can be located on the top or bottom of the main web 310 and/or the cutting filament 320 can line an edge of the main web 310. The cutting filament 320 and the main web 310 can held together by, but are not limited to being held together by, adhesive, pressure, friction, and/or small catches.

Figure 4:
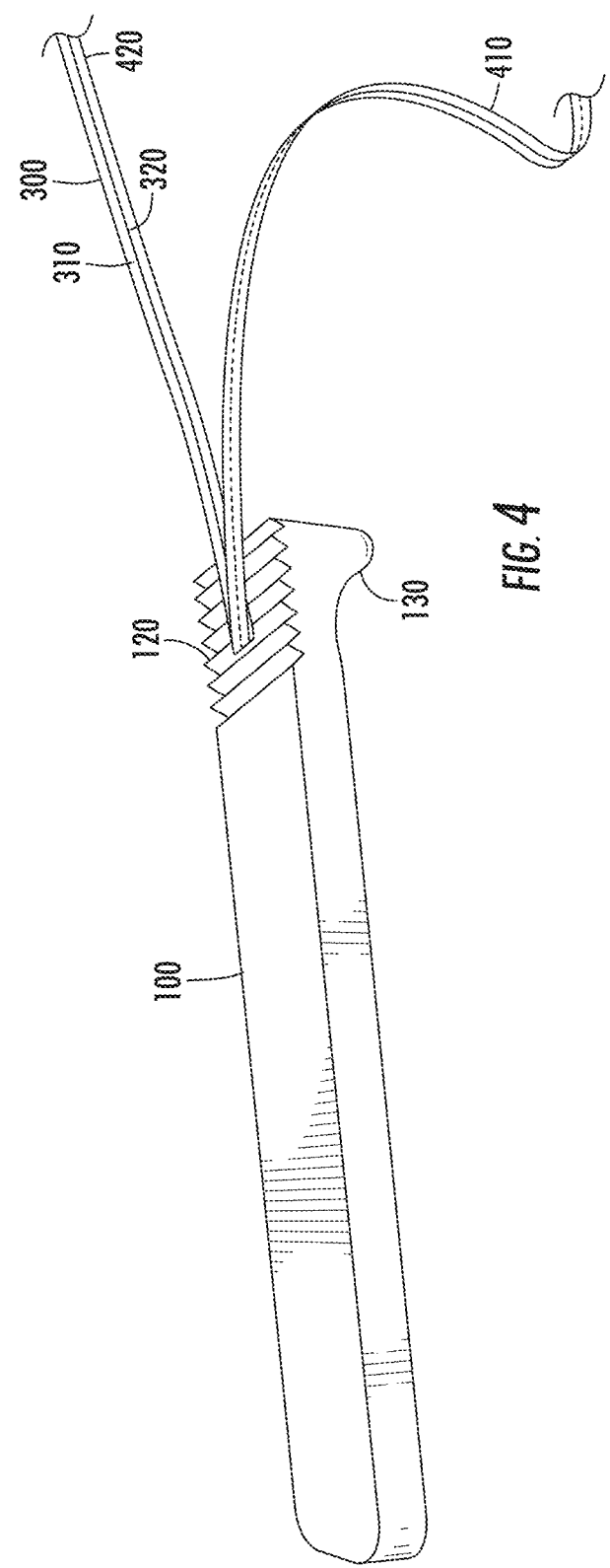
FIG. 4 is a perspective view of a filament tape utilization device and the filament tape before the cutting filament has been separated from the main web according to at least one embodiment of the present disclosure.

FIG. 4 shows a perspective view of placement of the filament tape 300 on the filament tape utilization device 100 in preparation for separating the cutting filament 320 from the main web 310 according to at least one embodiment of the present disclosure. As shown in FIG. 4, the filament tape 300 is folded and laid on top of the treads 120. The secured portion of the filament tape 420 is secured to a surface 710, as explained in more detail below. The free end of the filament tape 410 hangs loose from the filament tape utilization device 100. In other embodiments of the present disclosure, the filament tape 300 can be folded and laid on top of the support wall 130. In yet another embodiment of the present disclosure, the filament tape 300 can be folded and laid in between the two hinged handles 210.

Figure 5:
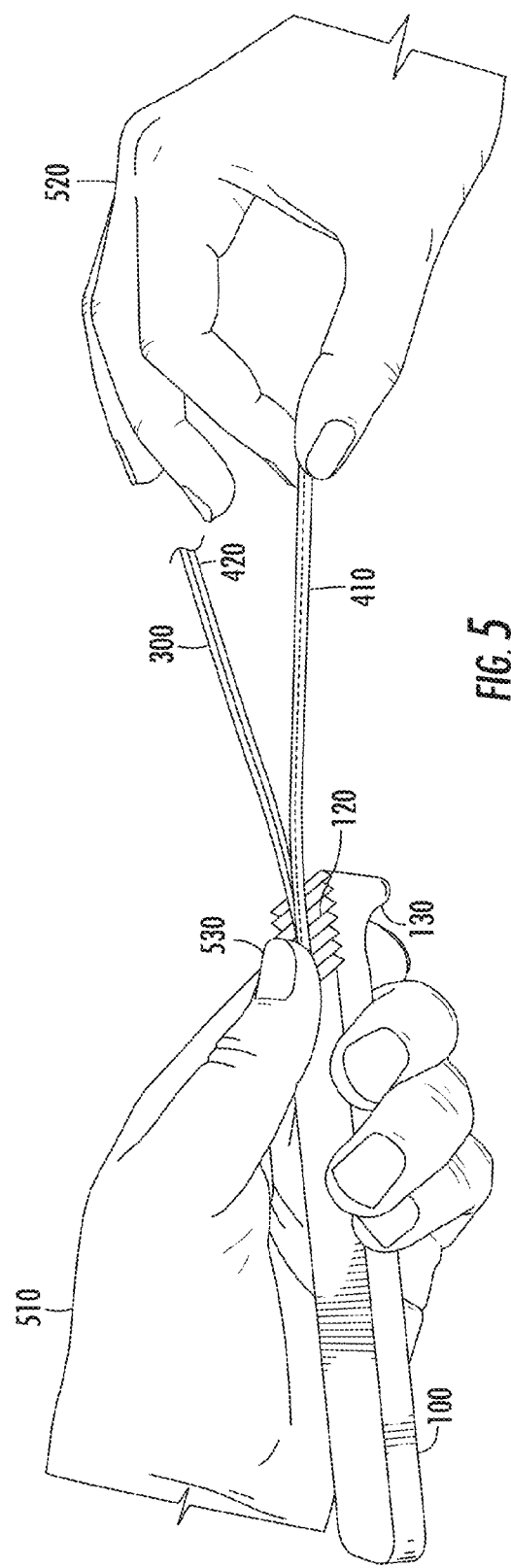
FIG. 5 is a perspective view of the filament tape utilization device, the filament tape, and a user's hands before the cutting filament has been separated from the main web according to at least one embodiment of the present disclosure.

FIG. 5 shows the perspective view of FIG. 4 with the addition of the user's device hand 510 and free hand 520 in further preparation for separating the cutting filament 320 from the main web 310 according to at least one embodiment of the present disclosure. As shown in FIG. 5, the device hand 510 holds the filament tape utilization device 100. The device hand thumb 530 holds the folded filament tape 300 firmly in place on top of the treads 120. The free hand 520 holds the loose end of the filament tape 300. In other embodiments of the present disclosure, the placement of the device hand 510 and free hand 520 may vary. For example, if the filament tape 300 is folded over the support wall 130, the device hand 510 then holds the folded filament tape 300 firmly in place on top of the support wall 130. In another embodiment, the device hand thumb 530 may be any finger. In another embodiment, the folded filament tape 300 may be held firmly in place by another object or tool. In another embodiment, the device hand 510 holds the hinged handles 210 of the filament tape utilization device 100 together to keep the folded filament tape 300 firmly in place between the two hinged handles 210. In yet another embodiment, the free hand 520 can be another object or tool that can securely hold the free end of the filament tape 410.

Figure 6:
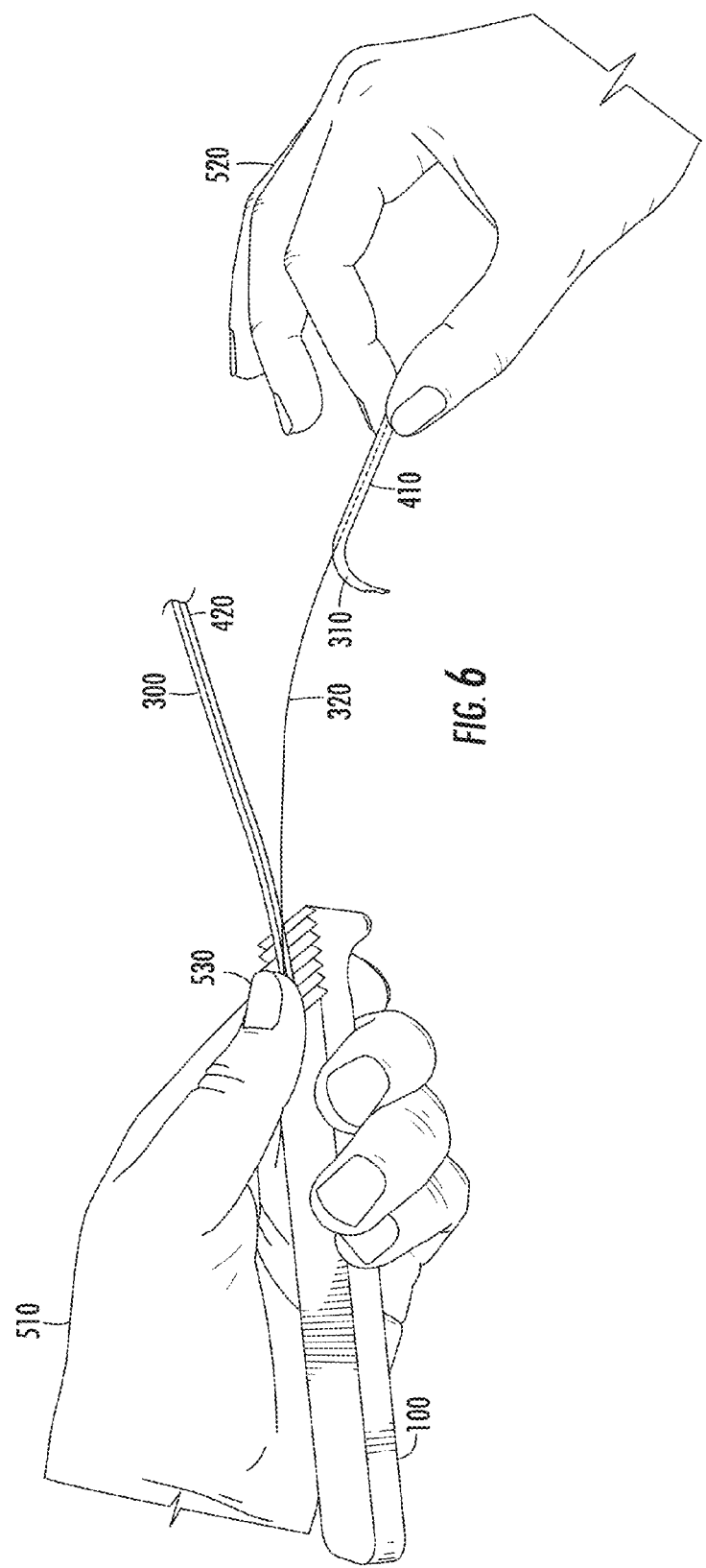
FIG. 6 is a perspective view of the filament tape utilization device, the filament tape, and a user's hands after the cutting filament has been separated from the main web according to at least one embodiment of the present disclosure.

FIG. 6 shows the perspective view of FIG. 5 after the cutting filament 320 has been successfully separated from the main web 310 according to at least one embodiment of the present disclosure. As shown in FIG. 6, the free end of the filament tape 410 is released from the secured portion of the filament tape 420, leaving the folded cutting filament 320 separate from the main web 310 and still secured by the device hand thumb 530. The separation is actuated when the free hand 520 pulls the free end of the filament tape 410 away from the filament tape utilization device 100. The force exerted by the free hand 520 on the firmly held folded filament tape 300 on the filament tape utilization device 100 shears the main web 310 and at least partially releases the main web 310 from the cutting filament 320. Once the free end of the filament tape 410 has been successfully at least partially separated from the secured portion of the filament tape 420, the free hand 520 can release the free end of the filament tape 410. In another embodiment of the present disclosure, the free end of the filament tape 410 is pulled by another object or tool.

Figure 7A:
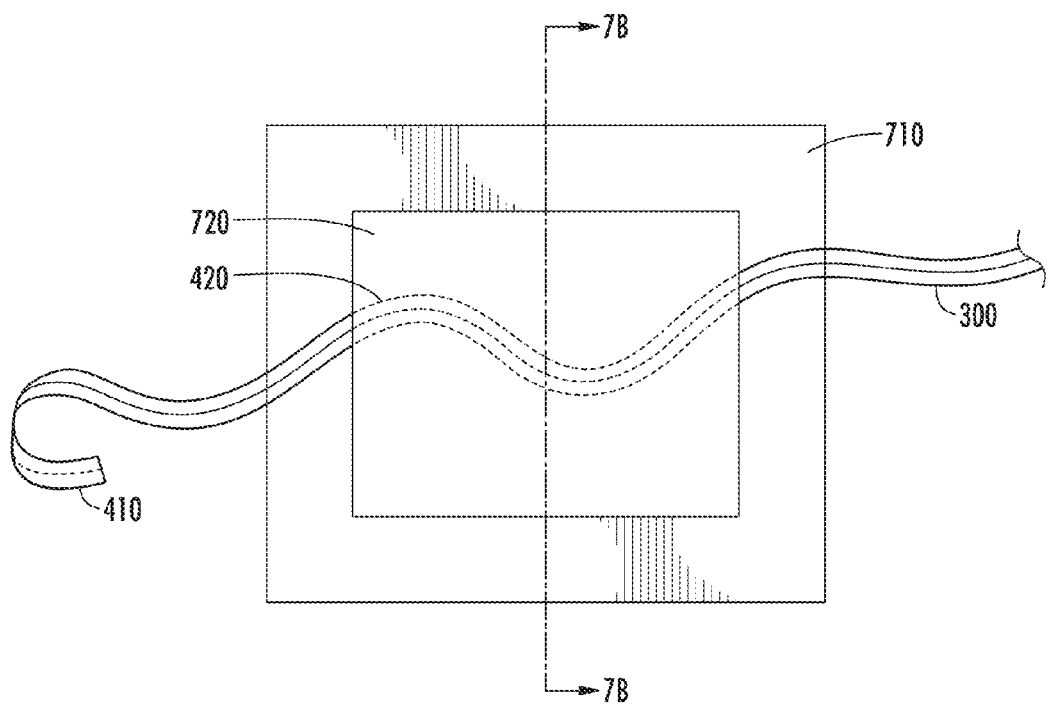
FIG. 7A is a view of the adhesive sheet material, filament tape, and surface, all viewed from the display side of the adhesive sheet material according to at least one embodiment of the present disclosure.

FIG. 7A shows a view of a surface 710 with filament tape 300 placed in a desired pattern underneath adhesive sheet material 720 according to at least one embodiment. FIG. 7A shows the adhesive sheet material 720, filament tape 300 and surface 710 as viewed by a user from the display side of the adhesive sheet material 710, i.e. top of the adhesive material 730. The surface 710 can vary in size, shape, and texture. The surface 710 can be, but is not limited to being, an automotive vehicle, a floor, a bicycle, a motorcycle, a commercial vehicle, a train, a boat, a sign, a window, a wall, or a door. The adhesive sheet material 720 can be, but is not limited to being, vinyl, vinyl-like polymers, and other flexible material that can be cut using filament tape 300. In other embodiments, the placement and design of the filament tape 300 varies depending on the user's desired pattern. In other embodiments, the placement of the filament tape 300 can relate to or be oriented in a desired relationship to specific features on the surface 710 that the user does or does not want to be covered in the adhesive sheet material 720. As shown in FIG. 7A, the free end of the filament tape 410 is hanging over the edge of the surface and the secured portion of the filament tape 420 is on top of the surface 710 and under the adhesive sheet material 720.

Figure 7B:
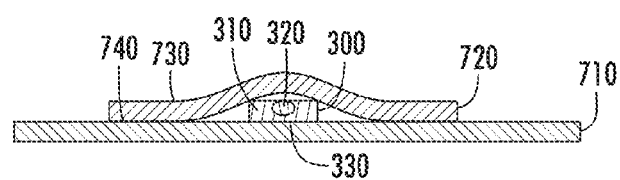
FIG. 7B shows a cross-sectional view taken at line A-A of FIG. 7A.

FIG. 7B shows a cross-sectional view AA of the embodiment shown in FIG. 7A across line A-A. As shown in FIG. 7B the filament tape 300 is placed on the surface 710 with the filament tape adhesive 330 mating with the surface 710. The filament tape 300 is shown with the cutting filament 320 in contact with the main web 310. The adhesive sheet material 720 is placed on the surface 710 over the filament tape 300. The adhesive sheet material 720 is placed on the surface 710 with the bottom of the adhesive sheet material 740 mating with the surface 710 and the top of the adhesive sheet material 730 facing opposite the bottom of the adhesive sheet material 740. The bottom of the adhesive sheet material 740 is adhesive and therefore allows the adhesive sheet material to stick to the surface 710. The top of the adhesive sheet material 730 can be, but is not limited to being, different colors, textures, patterns, and/or text.

Figure 8:
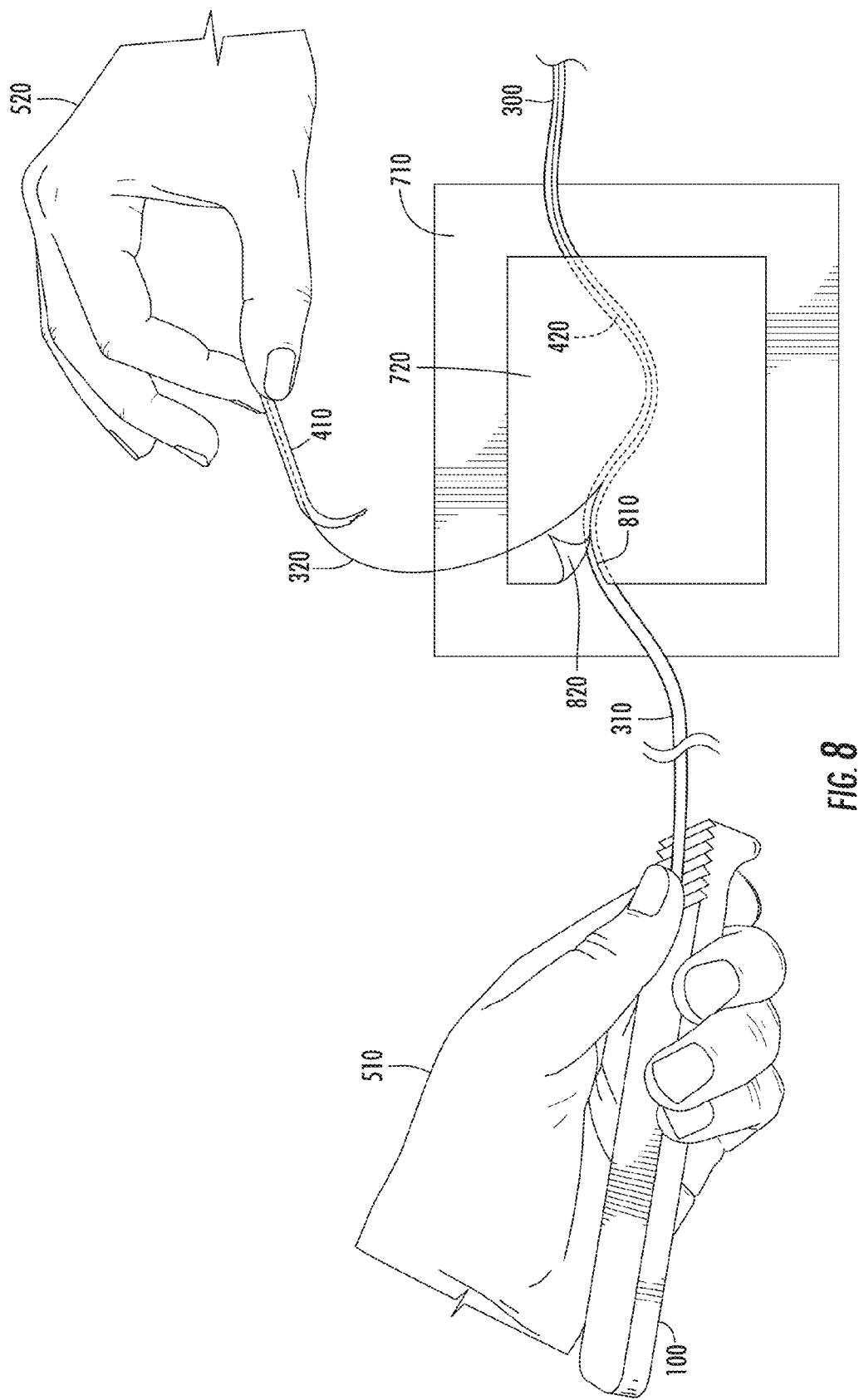
FIG. 8 is a perspective view of a filament tape utilization device as used with the filament tape to create a designed incision in the adhesive sheet material on the surface according to at least one embodiment of the present disclosure.

In one embodiment of the present disclosure, after the filament tape 300 is placed on the surface 710 in a desired position and/or pattern, and the adhesive sheet material 720 is placed on top of the filament tape 300 and surface 710, the filament tape 300 is folded over and secured to the filament tape utilization device 100. The cutting filament 320 is then separated from the main web 310 using the filament tape utilization device 100, as described above. FIG. 8 shows a perspective view of the filament tape utilization device 100 used in connection with the filament tape 300 to aid in the cutting of the adhesive sheet material 720 on the surface 710 according to one embodiment. As shown in FIG. 8, the user has already separated the cutting filament 320 from the main web 310 using the filament tape utilization device 100. The user then continues to pull the free end of the filament tape 410 with the free hand 520 lifting the cutting filament 320 through the adhesive sheet material 720 creating an incision 810, which allows the excess adhesive sheet material 820 to be lifted and removed from the surface 710. In another embodiment, after the cutting filament 320 has been separated from the main web 310 the user places either the treads 120 or support wall 130 of the filament tape utilization device 100 on the edge of the adhesive sheet material 720 and firmly holds the filament tape utilization device 100 in place while the free hand 520 initiates the first cut in the adhesive sheet material 720, thereby preventing unwanted tearing of the adhesive sheet material 720.

Figure 9:
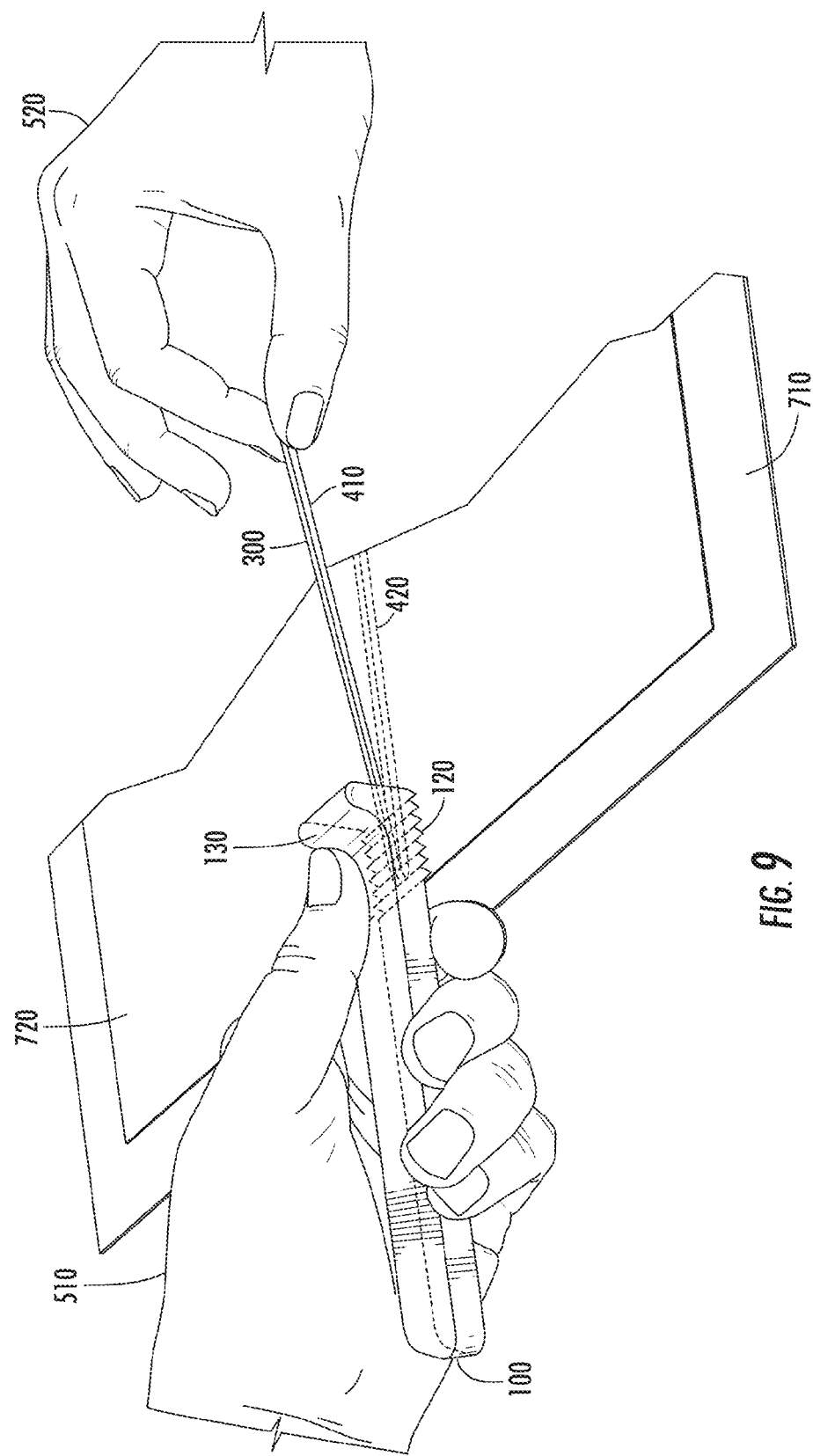
FIG. 9 is a perspective view of the filament tape utilization device, the adhesive sheet material, filament tape, surface, and a user's hands before the cutting filament has been separated from the main web according to at least one embodiment of the present disclosure.

FIG. 9 shows the filament tape utilization device 100 in use according to at least one embodiment of the present disclosure. As shown in FIG. 9, the filament tape 300 is on the surface 710 and the adhesive sheet material 720 covers a portion of the filament tape 300 on the surface 710. Said portion of the filament tape 300 is secured underneath the adhesive sheet material 720. At the edge of the adhesive sheet material 720 where the free end of the filament tape 410 begins, the free end of the filament tape 410 has been folded over the top of the adhesive sheet material 720 towards an interior portion of the adhesive sheet material 720. The filament tape utilization device 100 is placed over the free end of the filament tape 410 and the surface of the adhesive sheet material 720. The filament tape utilization device 100 is held firmly in place by the device hand 510. In one embodiment, the device hand 510 uses the support wall 130 for additional support, strength, and to prevent the device hand 10 form sliding. In another embodiment, the filament tape utilization device 100 can be placed over the filament tape 300 on the surface 710 outside of the adhesive sheet material 720 and held in place by the device hand 510. Said filament tape 300 under the filament tape utilization device 100 can be a single layer or folded. As shown in FIG. 9, the free hand 520 is holding the free end of the filament tape 410 in preparation for releasing or disengaging the cutting filament 320 from the main web 310. In another embodiment, a portion of the adhesive sheet material 720 is left free from the surface 710 and protrudes over a portion of the free end of the filament tape 410. In another embodiment, the filament tape utilization device 100 is used to secure portion of the free end of the filament tape 410 underneath the adhesive sheet material 720. At the edge of the free end of the adhesive sheet material 720 where the free end of the filament tape 410 begins, the free end of the filament tape 410 has been folded over the top of the adhesive sheet material 720 towards an interior portion of the adhesive sheet material 720. The device hand thumb 530 secures the folded free end of the filament tape 410 over the free end of the adhesive sheet material 720 and the free hand 520 holds the free end of the filament tape 410. In one embodiment, the free hand 520 pulls the free end of the filament tape 410 away from the filament tape utilization device 100 causing the cutting filament 320 to release from the main web 310, leaving the device hand 510 holding the filament tape utilization device 100 against the secured portion of the filament tape 420 and the free hand 520 holding the separated portion of the cutting filament 320. Once the free hand 520 is holding the separated portion of the cutting filament 320, the free hand 520 can pull the cutting filament 320 through the adhesive sheet material 720 and create an incision 810.

The filament tape utilization device 100 has industry specific mass marketing appeal due to the vast number of businesses including, but not limited to, graphics businesses, sign businesses, window tinting businesses, vehicle wrap businesses, vehicle body shops, vehicle paint businesses, automotive bed liner industries, home décor industries and automotive paint protection industries that regularly use filament tape 300. These businesses could benefit from the use of the filament tape utilization device 100 on a regular basis as it allows for an easier, more efficient method of releasing or disengaging the cutting filament 320 from the main web 310 and initiating the cutting process.

Figure 10:
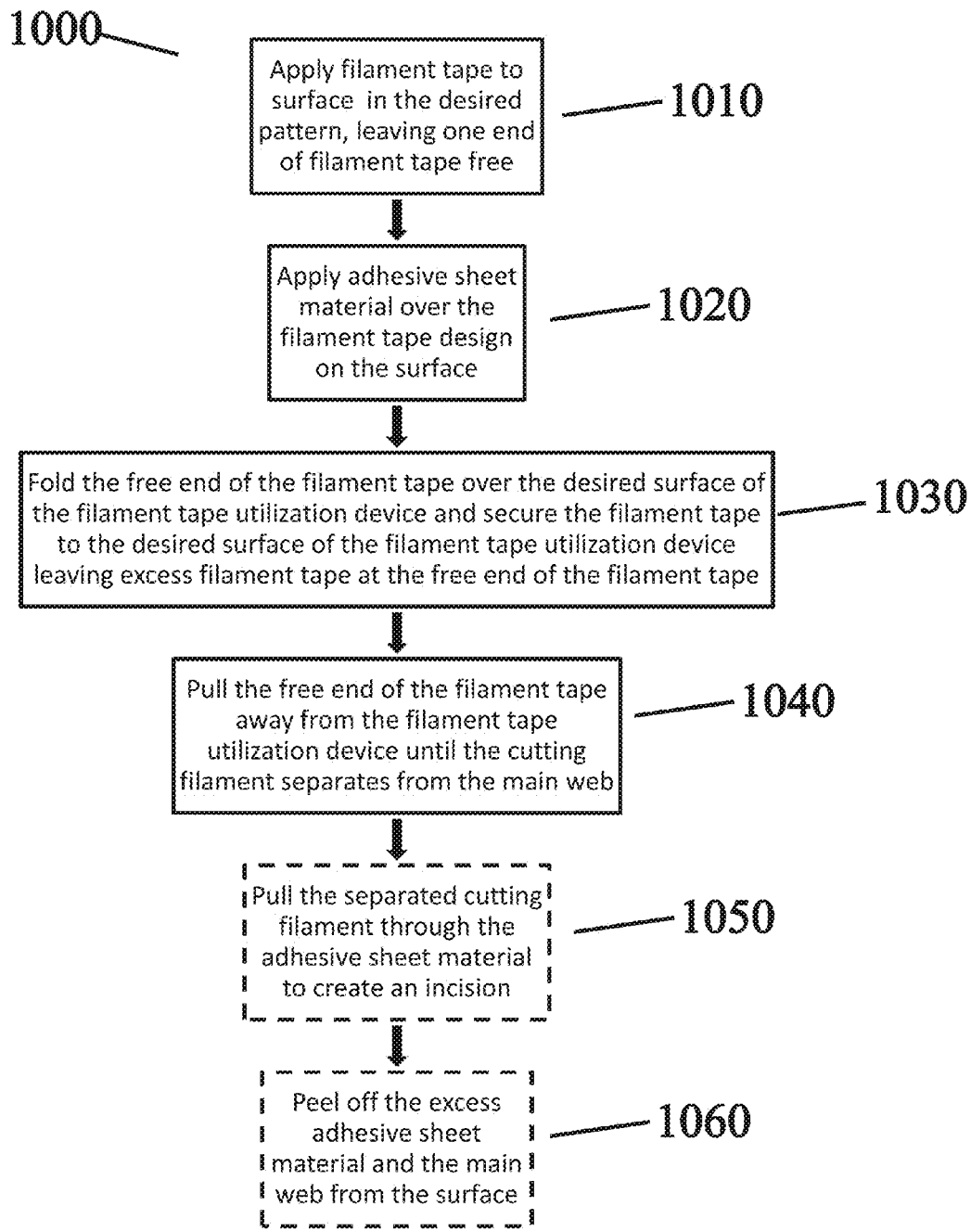
FIG. 10 shows a method of using a filament tape utilization device in at least one embodiment of the present disclosure.

FIG. 10 shows a method 1000 of using the filament tape utilization device 100 according to at least one embodiment of the present disclosure. The method 1000 includes the step 1010 of applying the filament tape 300 to a surface 710 in the desired pattern, leaving at least one end of the filament tape 300 free from the surface 710 to create the free end of the filament tape 410, and making sure there is a sufficient amount of excess filament tape 300 at the free end of filament tape 410 to allow a secure grip of the free end of the filament tape 410. In an embodiment, the sufficient amount of excess filament tape 300 at the free end of the filament tape 410 will be between two and twelve inches. The method 1000 also includes the step 1020 of applying the adhesive sheet material 720 over a portion of the filament tape 300 design on the surface 710, but not over the free end of the filament tape 410. The method 1000 further includes the step 1030 of folding the free end of the filament tape 410 over the desired surface of the filament tape utilization device 100, including, but not limited to either the treads 120 or support wall 130, and securing the free end of the filament tape 410 to the desired surface of the filament tape utilization device 100 leaving excess filament tape 300 at the free end. The method 1000 also includes the step 1040 of pulling the free end of the filament tape 300 away from the filament tape utilization device 100 until the cutting filament 320 disengages from the main web 310. The method 1000 further includes the optional step 1050 of pulling the separated cutting filament 320 through at least a portion of the adhesive sheet material 720 to create an incision 810. Step 1050 may optionally be done using the filament tape utilization device 100 to hold the cutting filament 320 and adhesive sheet material 720 when initiating the incision 810. The method 1000 may also include an optional step 1060 of peeling off the excess adhesive sheet material 720 and the main web 310 from the surface 710.

Figure 11:
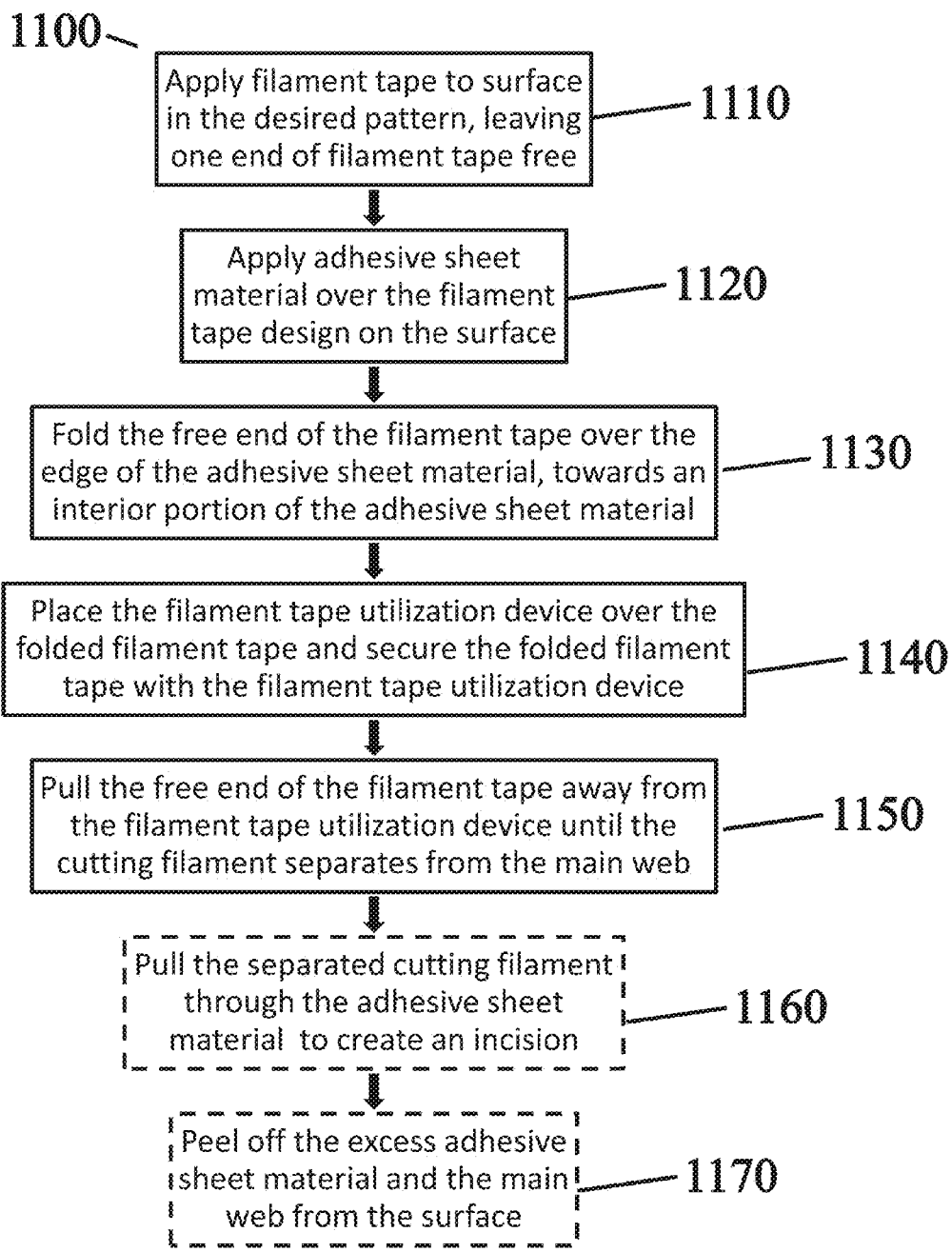
FIG. 11 shows a method of using a filament tape utilization device in at least one embodiment of the present disclosure.

FIG. 11 shows a method 1100 of using the filament tape utilization device 100 according to at least one embodiment of the present disclosure. The method 1100 includes the step 1110 of applying the filament tape 300 to a surface 710 in the desired pattern, leaving at least one end of the filament tape 300 free from the surface 710 to create the free end of the filament tape 410, and making sure there is a sufficient amount of excess filament tape 300 at the free end of filament tape 410 to allow the user to grip the free end of the filament tape 410 securely. In an embodiment, the sufficient amount of excess filament tape 300 at the free end of the filament tape 410 will be between two and twelve inches. The method 1100 also includes the step 1120 of applying the adhesive sheet material 720 over a portion of the filament tape 300 design on the surface 710, but not over the free end of the filament tape 410. The method 1100 further includes the step 1130 of folding a portion of the free end of the filament tape 410 over the edge of the adhesive sheet material 720, towards an interior portion of the adhesive sheet material 720. In another embodiment the user can fold the portion of the free end of the filament tape 410 on the surface 710 outside the adhesive sheet material 720. In yet another embodiment the user can place an unfolded, i.e. single layer, portion of the free end of the filament tape 410 on the surface 710 outside the adhesive sheet material 720. The method 1100 further includes the step 1140 of placing the filament tape utilization device 100 over the folded portion of the free end of the filament tape 410 and securing the filament tape 300 with the desired surface of the filament tape utilization device 100, including, but not limited to either the treads 120 or support wall 130. In another embodiment, the filament tape utilization device 100 is placed over the folded portion of the free end of the filament tape 410 on the surface outside of the adhesive sheet material 720 or over the unfolded, i.e. single layer, portion of the free end of the filament tape 410 on the surface outside of the adhesive sheet material 720, securing the filament tape 300 with the desired surface of the filament tape utilization device 100, including, but not limited to either the treads 120 or support wall 130. The method 1100 also includes the step 1150 of pulling the free end of the filament tape 300 away from the filament tape utilization device 100 until the cutting filament 320 disengages from the main web 310. The method 1100 further includes the optional step 1160 of pulling the separated cutting filament 320 through at least a portion of the adhesive sheet material 720 to create an incision 810. Step 1160 may optionally be done while the filament tape utilization device 100 is held in place on adhesive sheet material 720 to assist with starting the incision 810. The method 1100 may also include an optional step 1170 of peeling off the excess adhesive sheet material 720 and the main web 310 from the surface 710.

Figure 12:
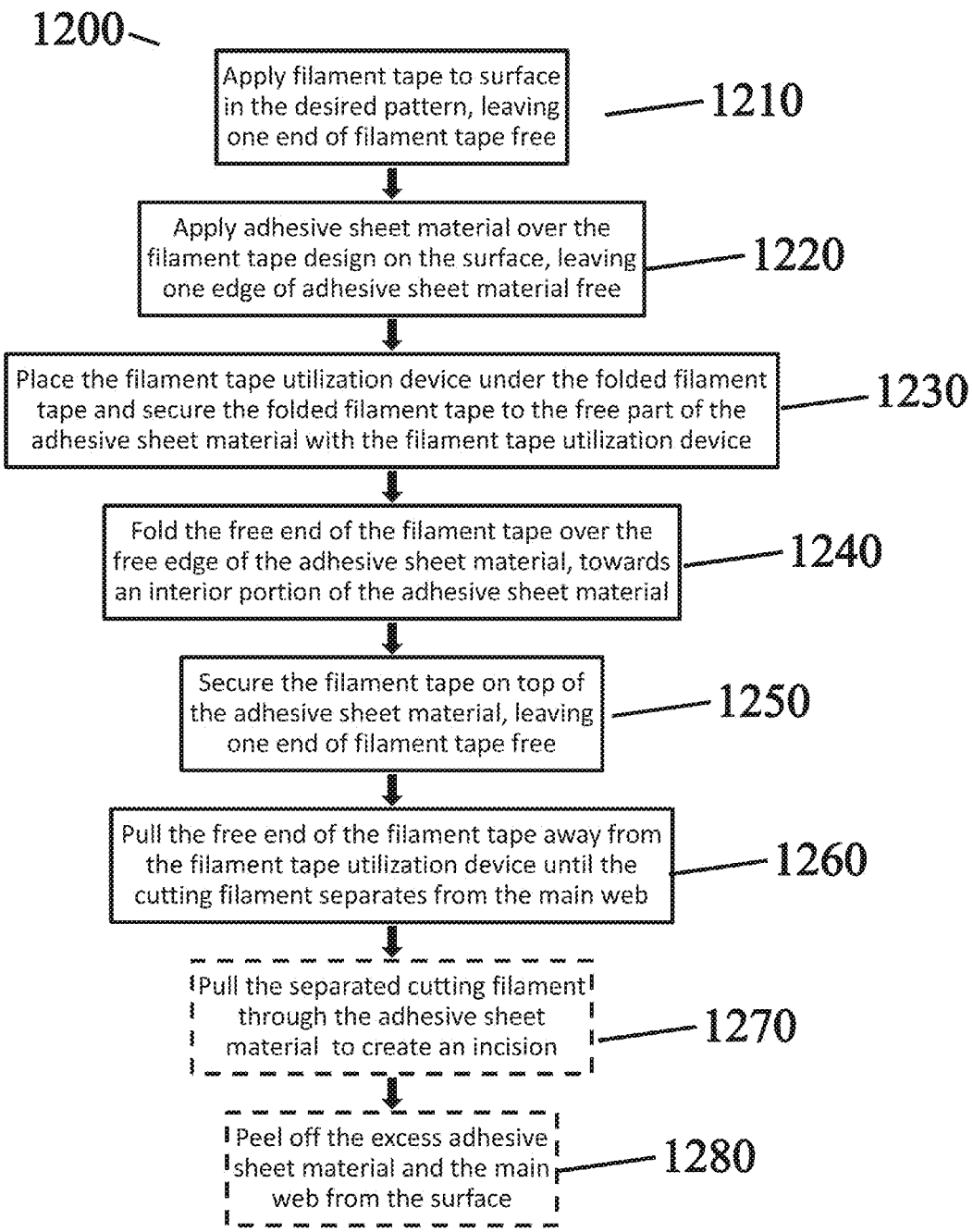
FIG. 12 shows a method of using a filament tape utilization device in at least one embodiment of the present disclosure.

FIG. 12 shows a method 1200 of using the filament tape utilization device 100 according to at least one embodiment of the present disclosure. The method 1200 includes the step 1210 of applying the filament tape 300 to a surface 710 in the desired pattern, leaving at least one end of the filament tape 300 free from the surface 710 to create the free end of the filament tape 410, and making sure there is a sufficient amount of excess filament tape 300 at the free end of filament tape 410 to allow the user to grip the free end of the filament tape 410 securely. In an embodiment, the sufficient amount of excess filament tape 300 at the free end of the filament tape 410 will be between two and twenty-four inches. The method 1200 also includes the step 1220 of applying the adhesive sheet material 720 over both the a portion of the filament tape 300 design on the surface 710 and over a portion over the free end of the filament tape 410, making sure to leave the portion of the adhesive sheet material 720 over the free end of the filament tape 410 free from the surface 710. The method 1200 further includes the step 1230 of placing the filament tape utilization device 100 near the edge of the free end of the adhesive sheet material 720 securing the portion of the free end of the filament tape 410 that is underneath the free end of the adhesive sheet material 720 with the desired surface of the filament tape utilization device 100, including, but not limited to either the treads 120 or support wall 130. The method 1200 further includes the step 1240 of folding a portion of the free end of the filament tape 410 over the edge of the free portion of the adhesive sheet material 720, towards an interior portion of the adhesive sheet material 720. The method 1200 further includes the step 1250 of securing the folded portion of the free end of the filament tape 410 over the edge of the free portion of the adhesive sheet material 720 in place with the device hand thumb 540, and making sure there is a sufficient amount of excess filament tape 300 at the free end of filament tape 410 to allow the user to grip the free end of the filament tape 410 securely. The method 1200 also includes the step 1260 of pulling the free end of the filament tape 300 away from the filament tape utilization device 100 until the cutting filament 320 disengages from the main web 310. The method 1100 further includes the optional step 1270 of pulling the separated cutting filament 320 through at least a portion of the adhesive sheet material 720 to create an incision 810. Step 1270 may optionally be done while the filament tape utilization device 100 is held in place on underneath the free end of the adhesive sheet material 720 when initiating the incision 810. The method 1200 may also include an optional step 1280 of peeling off the excess adhesive sheet material 720 and the main web 310 from the surface 710.

Figure 13:
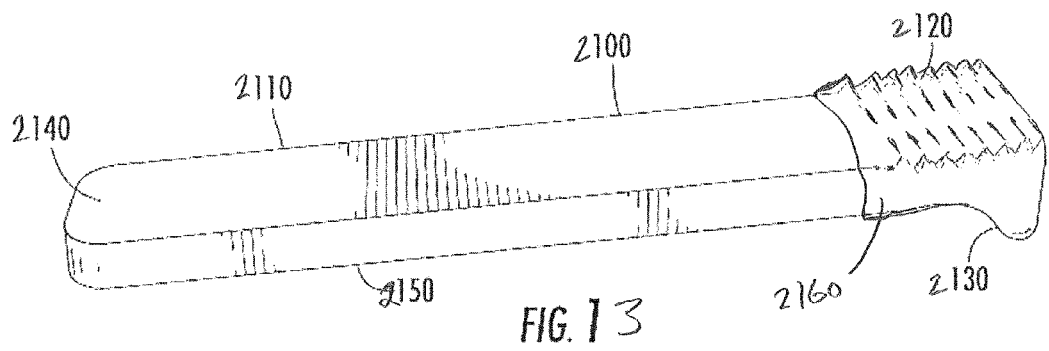
FIG. 13 is a perspective view of a tool in accordance with at least one embodiment of the present disclosure.
Figure 14:
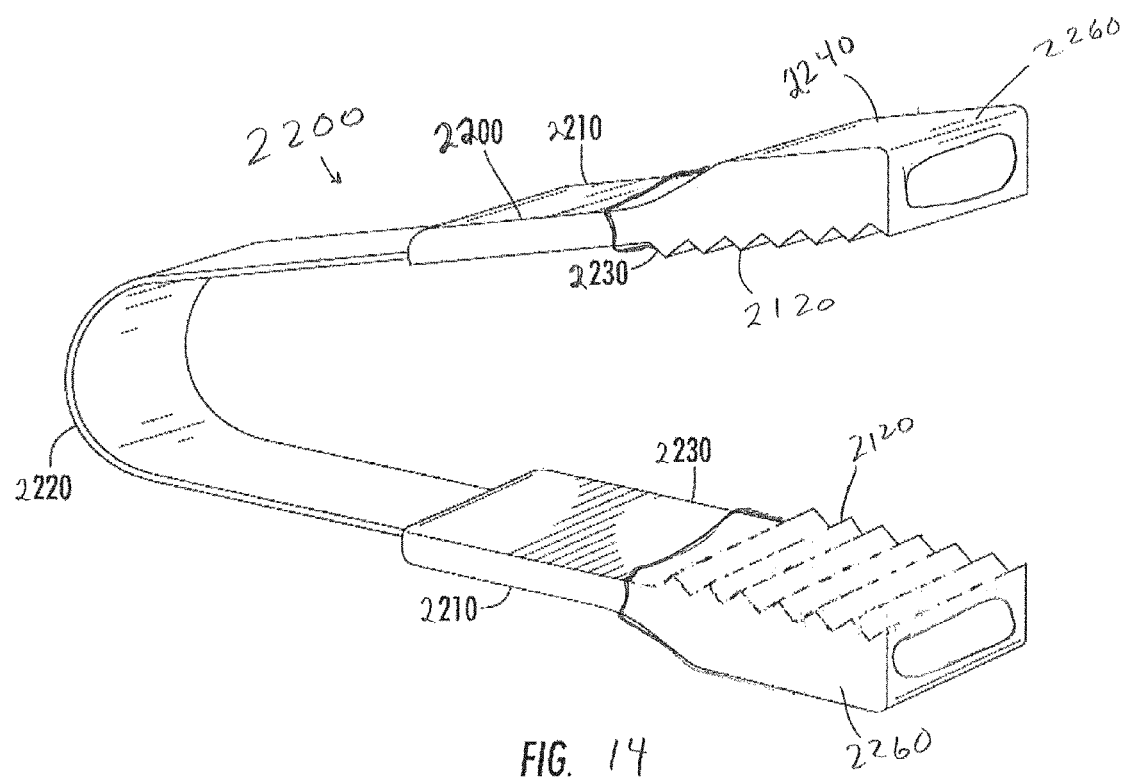
FIG. 14 is a perspective view of a tool according to at least one embodiment of the present disclosure.

Referring now to FIGS. 13 and 14, a filament tape utilization device or tool 2100 and a filament tape utilization device or tool 2200 according to embodiments of the present disclosure are illustrated. As described above with device 100 and/or any other tool or device described herein, the filament tape utilization devices 2100, 2200 are each made up of one or more types of material including, but not limited to, rubber, silicone, metal, wood, leather, plastic, bioplastic and/or a polymer. The filament tape utilization device 2100, 2200 can each be made of any strong flexible material that is capable of being shaped into a usable configuration. In one embodiment, the surface of the filament tape utilization device 2100, 2200 is textured to allow for additional traction when held in a user's hand. The texture can be, but is not limited to being, tacky, ruff, sticky, grainy, coarse, and/or gritty. In another embodiment, only the handle of the tool or device is textured.

As shown in FIG. 13, the filament tape utilization device 2100 has a handle 2110 to allow a user to hold the filament tape utilization device 2100. The handle 2110 can be a variety of shapes including, but not limited to, round, cylindrical, rectangular, flat, curved, and/or a combination of shapes. In one embodiment, the handle 2110 is ergonomic. In another embodiment, the handle 2110 has an outer layer, which is pliable and/or textured for added comfort and control.

As shown in FIG. 13, the handle 2110 has a first surface 2140 and a second surface 2150 and a first end and a second end. At the first end of the second surface 2150 there is a support wall 2130, which can be used to support a user's hand and prevent the user's hand from sliding. The support wall 2130 can be, but is not limited to being, curved or straight. The support wall 2130 can be, but is not limited to being, long or short and as wide as, wider than, or less wide than the handle 2110. In one embodiment the support wall 2130 extends form the second surface between 0.25 and one inches. In one embodiment, the support wall 2130 is located between the first and second ends of the handle 2110. In another embodiment, the filament tape utilization device 2100 does not have a support wall 2130. In one embodiment, as shown in FIG. 13, the surface of the first surface 2140 above the support wall 2130 has treads 2120. In another embodiment, the filament tape utilization device 2100 has both treads and a support wall, only a support wall, only treads, or neither. The treads 2120 can be, but are not limited to being, multiple peaks where each peak extends the entire width of the handle 2110 and each peak rises slightly above the first surface 2140. In one embodiment, there is only one tread 2120.

The device or tool 2100 includes a tread cover 2160 disposed over the one or more treads 2120. In an embodiment, the one or more treads 2120, the tread cover 2160, and/or the wall 2130 define the first end. The tread cover 2160 is made from an elastomeric or polymeric material and/or shrink-wrapped over the one or more treads 2120 in one or more embodiments. In an embodiment, the tread cover 2160 surrounds the first end of the tool or device 2100. The device or tool 2100 is made from aluminum or another metal in an embodiment, but may be made from a polymer, elastomer, ceramic, or another material in additional embodiments. The tread cover 2160 is removable and/or replaceable in an embodiment of the present disclosure. One or more methods of the present disclosure include covering the one or more treads 2120 with the tread cover 2160 and/or removing the tread cover 2160 from the device or tool 2100. Additionally, any feature, function, or method step related to any filament tape utilization device or tool described herein is included and/or describes the device or tool 2100 in one or more embodiments.

Referring again to FIG. 14, in another embodiment of the present disclosure, the filament tape utilization device 2200 has two handles 2210. The two handles 2210 are connected by a hinge 2220. The hinge 2220 can be, but is not limited to being, a flexible material, pivot hinge, or other suitable hinge known in the art. The hinge 2220 may also include a locking mechanism that allows a user to lock the two handles 2210 certain distances from each other. The hinge 2220 allows the two handles 2210 to mate at the end of the filament tape utilization device 2200 opposite the hinge 2220. The handle 2210 has an inner handle 2230 and an outer handle 2240. On the inner handle 2230 at the end of the handle 2210 opposite the hinge 2220 there are treads 2120. The treads 2120 on the two handles 2210 will mate when the hinge 2220 is in the closed position. In another embodiment, only one of the two handles 2210 has treads 2120. The outer handle 2240 allows for a user's hand to hold and use the filament tape utilization device 200. The handle 2210 can be a variety of shapes including, but not limited to, round, cylindrical, rectangular, flat, curved, and/or a combination of shapes. In one embodiment, the handle 2210 is ergonomic. In another embodiment, the handle 2210 has an outer handle 2240, which is pliable and/or textured for added comfort and control. In yet another embodiment, the hinge 2220 allows for rotation of the two handles 2210 away from each other so that one handle 2210 can be used alone.

The device or tool 2200 includes at least one tread cover 2260 disposed over the one or more treads 2120. In an embodiment, the one or more treads 2120, the at least one tread cover 2260, and/or the wall 2230 define the first end. In the embodiment illustrated in FIG. 14, two tread covers 2260 cover the two illustrated sets of one or more treads 2120. The tread cover 2260 is made from an elastomeric or polymeric material and/or shrink-wrapped over the one or more treads 2120 in one or more embodiments. In an embodiment, the tread cover 2260 surrounds the first end of the tool or device 2200. The device or tool 2200 is made from aluminum or another metal in an embodiment, but may be made from a polymer, elastomer, ceramic, or another material in additional embodiments. The tread cover 2260 is removable and/or replaceable in an embodiment of the present disclosure. One or more methods of the present disclosure include covering the one or more treads 2120 with the tread cover 2260 and/or removing the tread cover 2260 from the device or tool 2200. Additionally, any feature, function, or method step related to any filament tape utilization device or tool described herein is included and/or describes the device or tool 2200 in one or more embodiments.

While various embodiments of a filament tape utilization device and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

What is claimed is:

1. A tool comprising:
   at least one handle comprising
      a first surface;
      a second surface opposite the first surface;
      a first end; and
      a second end opposite the first end;
   at least one tread disposed at the first surface and the first end and comprising at least one peak extending above the first surface and across the at least one handle;
   a wall extending from the second surface and originating at the first end; and
   a tread cover disposed over the at least one tread, wherein the at least one tread and the wall define the first end.

2. The tool of claim 1, wherein the wall is as wide as the at least one handle.

3. The tool of claim 1, wherein the at least one tread comprises a plurality of treads extending across the handle.

4. The tool of claim 3, wherein the plurality of treads extend between 0.04 and 0.2 inches above the first surface.

5. The tool of claim 1, wherein the wall is curved toward the second end.

6. The tool of claim 1, wherein the wall extends from the second surface at least 0.25 inches.

7. The tool of claim 1, wherein the at least one handle includes two handles connected by a hinge.

8. The tool of claim 7, wherein the hinge includes a pivot hinge.

9. The tool of claim 7, wherein the hinge includes a flexible material.

10. The tool of claim 7, further comprising a locking mechanism.

11. The tool of claim 1, wherein the tread cover is shrink-wrapped over the first end.

12. A tool comprising:
   at least one handle comprising
      a handle width;
      a first surface;
      a second surface opposite the first surface;
      a first end; and
      a second end opposite the first end;
   at least one tread disposed at the first surface and the first end and extending above the first surface and across the handle width; and
   a tread cover disposed over the at least one tread, wherein the at least one tread and the tread cover define the first end.

13. The tool of claim 12, wherein the at least one tread extends between 0.04 and 0.2 inches above the first surface.

14. The tool of claim 12, further comprising a wall extending from the second surface, originating at the first end, and having a wall width equal to the handle width, wherein the at least one tread, the tread cover, and the wall define the first end.

15. The tool of claim 14, wherein the wall is curved toward the second end.

16. The tool of claim 14, wherein the wall extends from the second surface at least 0.25 inches.

17. The tool of claim 12, wherein the at least one handle includes two handles connected by a hinge.

18. The tool of claim 17, wherein the hinge includes a pivot hinge.

19. The tool of claim 17, wherein the hinge includes a flexible material.

20. The tool of claim 17, further comprising a locking mechanism.

* * * * *